United States Patent [19]
Pirkle et al.

[11] Patent Number: 5,578,212
[45] Date of Patent: Nov. 26, 1996

[54] CHIRAL SELECTOR USEFUL FOR SEPARATION OF ENANTIOMERS OF β-AMINO ALCOHOL COMPOUNDS

[75] Inventors: William H. Pirkle, Champaign; Won-jae Lee, Urbana, both of Ill.

[73] Assignee: Research Corporation Technologies, Inc., Tucson, Ariz.

[21] Appl. No.: 981,637

[22] Filed: Nov. 25, 1992

Related U.S. Application Data

[63] Continuation-in-part of Ser. No. 761,212, Sep. 17, 1991, Pat. No. 5,254,258.

[51] Int. Cl.$^6$ ............................................. B01D 61/38
[52] U.S. Cl. .................... 210/638; 210/643; 210/650; 210/656
[58] Field of Search ............................ 210/650, 198.2, 210/635, 638, 644, 656; 502/401; 556/400

[56] References Cited

U.S. PATENT DOCUMENTS

| | | | |
|---|---|---|---|
| 4,590,167 | 5/1986 | Gunther et al. | 210/658 X |
| 5,080,795 | 1/1992 | Pirkle et al. | 210/643 |
| 5,290,440 | 3/1994 | Pirkle et al. | 210/644 X |

OTHER PUBLICATIONS

Pirkle, et al., "A Widely Useful Chiral Stationary Phase for the High–Performance Liquid Chromatography Separation of Enantiomers", *103 J. Am. Chem. Soc.*, 3964–66 (1981).
Pettersson, et al., "Separation of Enantiomeric Amines by Ion–Pair Chromatography", *204 J. Chromatogr.*, 179–83 (1981).
Pirkle, et al., "A Rational Approach to the Design of Highly–Effective Chiral Stationary Phasers", *316 J. Chromatogr.*, 585–604 (1984).
Wainer, et al., "The Direct Enantiomeric Determination of (–)– (+)– Propanolol in Human Serum by High–Performance Liquid Chromatography on a Chiral Stationary Phase", *306 J. Chromatogr.*, 405–11 (1984).
Armstrong, et al., "Separation of Drug Stereoisomers by the Formation of B–Cyclodextrin Inclusion Complexes", *232 Science*, 1132–35 (1986).
Okamoto, et al., "Optical Resolution of B–Blockers by HPLC on Cellulose Triphenylcarbamate Derivatives", *Chem. Lett.*, 1237–40 (1986).
Pirkle, et al., "Intermolecular $^1H[^1H]$ Nuclear Overhauser Effects in Diastereomeric Complexes: Support for a Chromatographically Derived Chiral Recognition Model", *108 J. Am. Chem. Soc.*, 5627–28 (1986).
Petterson, et al., "Influence of Enantiomeric Purity of Chiral Selector on Stereoselectivity", *407 J. Chromatogr.*, 217–29 (1987).
Pirkle, et al., "Reciprocity in Chiral Recognition Comparison of Several Chiral Stationary Phases", *404 J. Chromatogr.*, 107–15 (1987).
Pirkle, et al., "Systematic Studies of Chiral Recognition Mechanisms," 23–35 in *Chiral Separations*, Stevenson, et al., ed. (1988).
Aboul–Enein, et al., "Direct High–Performance Liquid Chromatographic Separation of Penbutolol Enantiomers on a Cellulose Tris–3, 5–dimethylyphenyl Carbamate Chiral Stationary Phase", *1 Chirality*, 301–04 (1989).

(List continued on next page.)

*Primary Examiner*—Frank Spear
*Attorney, Agent, or Firm*—Scully, Scott, Murphy & Presser

[57] ABSTRACT

The present invention relates to the separation of β-amino alcohol compounds, particularly compounds known as β-blockers, by employing what is known as a chiral selector compound which can achieve separation of enantiomers without requiring derivatization of the enantiomers before effecting separation.

29 Claims, 5 Drawing Sheets

OTHER PUBLICATIONS

Hermansson, "Enantiomeric Separation of Drugs and Related Compounds Based on their Interaction with $\alpha_1$-acid Glycoprotein", *8 Anal. Chem.*, 251–59 (1989).

Moriguchi, et al., Abstract of Paper M/TU-P-017, "Liquid Chromatographic Separation of Enantiomers Upon Chiral Stationary Phases Comprised of (D)-N-(3,5-Dinitrobenzoyl)-Penicillamine", The Thirteenth Symposium on Column Liquid Chromatography (1989).

Pirkle, et al., "Preparation of Chiral Stationary Phase From an $\alpha$-Amino Phosphonate", *1 Chirality*, 57–62 (1989).

Walhagen, et al., "Coupled-Column Chromatography on Imobilized Protein Phases for Direct Separation and Determination of Drug Enantiomers in Plasma", *473 J. Chromatogr.*, 371–79 (1989).

Erlandsson, et al., "Immobilized Cellulase (CBH I) as a Chiral Stationary Phase for Direct Resolution of Enantiomers", *112 J. Am. Chem. Soc.*, 4573–74 (1990).

Regis Chemical Company Catalog, Sec. 5, 42–54 (1990).

Pirkle, W. H., et al. "Chiral Stationary Phase Designed for $\beta$-Blockers", *557 J. Chromatogr.*, 173–85 (Sep. 20, 1991).

Pirkle, W. H., et al., "A Rational Approach to the Design of Highly Effective Chiral Stationary Phases for the Liquid Chromatographic Separation of Enantiomers", *2(2) J. Pharma. Biol. Anal.*, 173–181 (1984).

Patent Abstracts of Japan, 15:No. 445 (C-884) and JP,A, 03190827 (Nippon Steel Corp.) Aug. 20, 1991.

Pirkle et al. (1988) "An Improved Chiral Stationary Phase for the Facile Separation of Enantiomers", *Journal of Chromatography* vol. 144, No. 2, pp. 311–322.

T = 21°C
$\alpha$ = 1.39
$k_1'$ = 4.46

T = 0°C
$\alpha$ = 1.63
$k_1'$ 1.86

T = -24°C
$\alpha$ = 2.11
$k'$ = 1.28

CHIRAL SELECTOR USEFUL FOR SEPARATION OF ENANTIOMERS OF β-AMINO ALCOHOL COMPOUNDS

The invention described herein was made with Government support under Grant NSF CHE 87-14950 awarded by the National Science Foundation. The Government has certain rights in the invention.

CROSS-REFERENCE TO RELATED APPLICATION

This application is a continuation-in-part of application Serial No. 761,212, filed Sep. 17, 1991, now U.S. Pat. No. 5,254,258.

BACKGROUND OF THE INVENTION

1. Field of the Invention

This invention relates to the separation of enantiomers. This invention more particularly relates to a chiral selector for separation of enantiomers. This invention especially relates to a chiral selector useful, for example, as a chiral stationary phase (CSP) in the liquid chromatographic (HPLC) separation of enantiomers of underivatized beta-amino alcohol compounds.

2. Description of the Prior Art

Stereoisomers are those molecules which differ from each other only in the way their atoms are oriented in space. Stereoisomers are generally classified as diastereomers or enantiomers; the latter embracing those which are mirror-images of each other, the former being those which are not. The particular arrangement of atoms that characterize a particular stereoisomer is known as its optical configuration, specified by known sequencing rules as, for example, either + or − (also D or L) and/or R or S.

Though differing only in orientation, the practical effects of stereoisomerism are important. For example, the biological and pharmaceutical activities of many compounds are strongly influenced by the particular configuration involved. Indeed, many compounds are only of widespread utility when provided in a given stereoisomeric form. Living organisms usually produce only one enantiomer of a pair. Only (−)-2-methyl-1-butanol is formed in yeast fermentation of starches; only (+)-lactic acid is formed in the contraction of muscle; fruit juices contain only (−)-malic acid and only (−)-quinine is obtained from a cinchona tree. In biological systems, stereochemical specificity is the rule rather than the exception, since the catalytic enzymes which are so important in such systems are optically active. The sugar (+)-glucose plays an important rule in animal metabolism and is the basic raw material in the fermentation industry; yet (−)-glucose is not metabolized by animals or fermented by yeasts. The mold Penicillium glaucum will only consume the (+)-enantiomer of an enantiomeric mixture of tartaric acid leaving (−)-tartaric acid intact. Only one stereoisomer of chloromycetin is an antibiotic. Not only does (+)-ephedrine not have any drug activity, but it interferes with the drug activity of its enantiomer. (−)-Carvone provides oil of spearmint with its distinctive odor while its enantiomer, (+)-carvone has the essence of caraway. Hence, it is desirable and often essential to separate stereoisomers to provide the useful version of an optically active chemical compound.

When diastereomers are involved, separation is generally not a significant problem because diastereomers have different physical properties, such as melting points, boiling points, solubilities in a given solvent, densities, refractive indices, etc. Hence, diastereomers may normally be separated from each other by conventional methods, such as fractional distillation, fractional crystallization, or chromatography.

Enantiomers, on the other hand, present a special problem because their physical properties are identical. They cannot as a rule—especially when in the form of a racemic mixture—be separated by ordinary methods: not by fractional distillation, because their boiling points are identical; not by conventional fractional crystallization, because (unless the solvent is optically active) their solubilities are identical; not by conventional chromatography because (unless the adsorbent is optically active) they are held equally onto the adsorbent. The problem of separating enantiomers is further exacerbated by the fact that conventional synthetic techniques almost always produce a mixture of enantiomers. When the mixture comprises equal amounts of enantiomers having different optical configurations, it is called a racemate or a racemic modification; and separation of the racemate into its respective enantiomers—this separation being generally known as a resolution—is, therefore, a process of considerable importance.

Various techniques for separating enantiomers are known. Most, however, are directed to small analytical quantities, meaning that, other drawbacks aside, when applied to preparative scale amounts (the milligram to kilogram range) a loss of resolution occurs. Hand separation—the oldest method of resolution—is not only impractical but can almost never be used since racemates seldom form mixtures of crystals recognizable as mirror-images.

Another method, known as an indirect separation, involves the conversion of a mixture of enantiomers—the racemate—into a mixture of diastereomers. The conversion is accomplished by reacting the enantiomers with an optically pure chiral derivatizing agent. The resultant diastereomers are separated from each other by taking advantage of their different physical properties. Once separated, by, for example, fractional crystallization, or more commonly, chromatography, the diastereomers are reconverted back into the corresponding enantiomers, which are now optically pure. Though achieving the requisite separation, the indirect method suffers in that it is time-consuming and can require large quantities of optically pure derivatizing agent which can be expensive and is oftentimes not recoverable. Moreover, the dederivatization step may itself result in racemization thus defeating the purpose of the separation earlier achieved.

A more current method which avoids some of the drawbacks attendant the indirect method is known as the direct method of separation. The direct method, much like the indirect method, involves the formation of a diastereomeric species. However, unlike the indirect method, this species is transient, with the stability of one species differing from the other.

In one application of the direct method, the mixture of enantiomers is allowed to interact with a chiral stationary phase (CSP), which, for example, could reside in a chromatographic column. The enantiomer that interacts more strongly with the chiral stationary phase than the other will have a longer residence time on the chiral stationary phase and hence a separation will occur. When the mode of interaction with the chiral stationary phase can be characterized, the elution order may be predicted. Examples of chiral stationary phases include those based on (L)-N-(3,5-dinitrobenzoyl)leucine, which is useful in separating enantiomers of N-aryl derivatized amino acids and esters and those based on (L)-N-(1-naphthyl)leucine which has been used to effectively separate N-(3,5-dinitrobenzoyl) derivatized amino compounds. HPLC columns packed with silica-bonded CSPs of a variety of pi-electron acceptors and pi-electron donors, including derivatives of phenylglycine, leucine, naphthyl-alanine and naphthylleucine are commercially available from Regis Chemical Company, Morton Grove, Ill.

In another application of the direct method, disclosed in U.S. Pat. No. 5,080,795 to Pirkle et al., enantiomers of such compounds as amino acids, amino esters, sulfonides, alcohols, amines, sulfonic acids or derivatives thereof are separated by means of a liquid membrane containing a chiral carrier, such as derivatized amino acid, (S)-N-(1-naphthyl)leucine octadecyl ester. The chiral carrier is capable of forming a stable complex with one of the enantiomers. The liquid membrane is located on one side of a semi-permeable barrier, and the mixture of enantiomers is located on the other side of the liquid membrane. The liquid membrane containing the chiral carrier impregnates the semi-permeable barrier under conditions effective to permit or cause a stable complex between the chiral carrier and one of the enantiomers to form in the liquid membrane. The liquid membrane containing the stable complex is passed to a second location where the conditions are effective to dissociate the stable complex and the recovery of the complex-forming enantiomer. In one embodiment of this application, a hollow-fiber membrane is employed as the semi-permeable barrier.

It is widely recognized that stereoisomers of pharmaceutical agents may have drastically different pharmacological potencies or actions. For example, the so-called β-blockers, widely used in the treatment of angina pectoris and hypertension, differ considerably in the physiological responses they elicit. Typically, the (S) enantiomers are 50–500 fold more active than their antipodes and may differ also in the nature of the elicited responses. β-blockers are adrenergic blocking agents capable of blocking nerve impulses to special sites (beta acceptors) in the cerebellum in order to reduce the heartbeat rate and the force of heart contractions. Owing to their importance, many potential β-blockers have been developed and tested, and a number are now marketed. Known β-blockers include compounds identified as metoprolol, oxprenolol, propanolol, pindolol, pronethalol and bufuralol. The common aspect of the compounds is that they all have a β-amino alcohol structure.

In the present scientific climate, all stereoisomers of a potential pharmaceutical must be evaluated individually. Consequently, methods of preparatively separating β-blocker stereoisomers and for ascertaining their stereochemical purity are of considerable current interest. Moreover, much effort continues to be expended by pharmacologists in the study of how β-blocker stereochemistry influences the extent and mode of their action. There are now a variety of liquid chromatographic methods which facilitate determinations of stereochemical purity of β-blockers, studies of differences in the rate of metabolism of their enantiomers and studies of the stereochemical pathways of metabolism. While it is possible and often practical to derivatize enantiomers with a chiral reagent so as to obtain diastereomers which are separable on an achiral column, there are potential disadvantages to this approach. In some instances, the enantiomers of β-blockers have been separated on achiral columns through the use of chiral mobile phase additives as reported by C. Petterson, et al. in *J. of Chromatogr.*, 204, 179–384 (1981) and 407, 217–229 (1987). However, the scope of this method remains undetermined, and it too is disadvantageous in some applications. Instances of derivatization with an achiral reagent prior to enantiomer separation on a column containing chiral stationary phases, CSPs, have been reported. However, the need for derivatization, and in the case of preparative separations—dederivatization, is an obstacle to be avoided if possible. The direct separation of underivatized enantiomers on a CSP is to be preferred but is neither always possible nor feasible.

The object of this invention is to provide a process for the separation of underivatized enantiomers of β-amino alcohol compounds, particularly β-blocker drugs.

Another object of this invention is to provide a process for the direct separation of underivatized enantiomers of β-amino alcohol compounds, particularly β-blocker drugs, by means of a chiral selector.

A further object of this invention is to provide a process for the direct separation of underivatized enantiomers of β-amino alcohol compounds, particularly β-blocker drugs, by means of liquid chromatography employing a chiral selector as a chiral stationary phase (CSP).

Yet another object of this invention is to provide a process for the direct separation of underivatized enantiomers of β-amino alcohol compounds, particularly β-blocker drugs, by means of a liquid membrane containing a chiral selector passing in contact with one side of a semi-permeable membrane while a mixture of the enantiomers are in contact with the other side of the semi-permeable membrane.

SUMMARY OF THE INVENTION

Briefly, the objects of this invention are achieved, by employing a chiral selector having a particular formula so as to provide a series of three bonding sites compatible with corresponding sites on one of the enantiomers of the subject β-amino alcohol compound for which separation is desired.

Two distinct groups of chiral selectors may usefully be employed in the subject invention. The chiral selector of the first group is a chemical compound having the formula

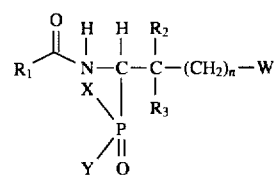

wherein
R$_1$ is

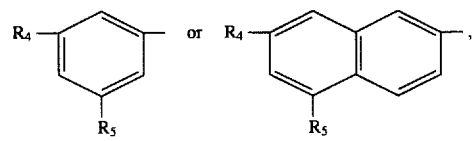

preferably
R$_1$ is

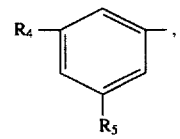

and $R_2$ $R_3$ are each independently lower alkyl, preferably methyl;

$R_4$ and $R_5$ are each independently $NO_2$, $N(R_6)_3^+$, CN, $COOR_7$, $SO_3H$ or $COR_8$, preferably $NO_2$;

$R_6$, $R_7$ and $R_8$ are each independently hydrogen or lower alkyl, preferably hydrogen or methyl, W is H or $CH=CH_2$, X and Y are each independently $OR_9$ or $NR_{10}R_{11}$, preferably X and Y are the same and most preferably X and Y are each $OR_9$, or X and Y together with the P to which they are attached form a 5- or 6-membered ring having the formula:

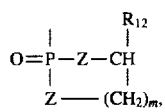

$R_9$, $R_{10}$, $R_{11}$ and $R_{12}$ are each independently hydrogen or lower alkyl, $R_9$ is preferably methyl, $R_{10}$, $R_{11}$ and $R_{12}$ are preferably hydrogen or methyl, Z is O or NH, n is 1 to 20, preferably 1 to 8 when W is H, and 1 to 3 when W is $CH=CH_2$, and m is 1 or 2, said compound being an R or an S enantiomer or a mixture of R and S enantiomers.

The chiral selector of the second group is a chemical compound having the formula:

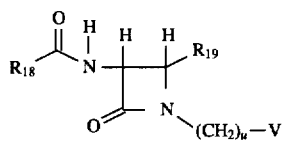

II wherein $R_{18}$ is

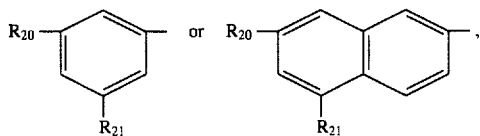

preferably $R_{18}$ is

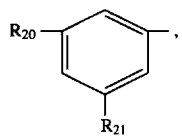

$R_{19}$ is lower alkyl or aryl, preferably t-butyl, phenyl or α-naphthyl, $R_{20}$ and $R_{21}$ are each independently $NO_2$, $N(R_{22})_3^+$, CN, $COOR_{23}$, $SO_3H$ or $COR_{24}$, preferably $NO_2$, $R_{22}$, $R_{23}$ and $R_{24}$ are each independently hydrogen or lower alkyl, preferably hydrogen or methyl, V is H or $CH=CH_2$, u is 1 to 20, preferably 1 to 11, said compound being an R or an S enantiomer or a mixture of R and S enantiomers.

In an embodiment of the subject invention, either of the above chiral selectors is employed in a process of separating enantiomers of a β-amino alcohol compound which comprises contacting a mixture of enantiomers of a first compound having a first and a second optical configuration and having the formula:

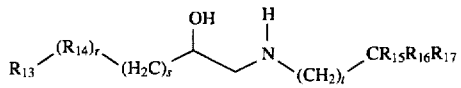

wherein $R_{13}$ is aryl or a nitrogen, sulfur or oxygen containing heterocyclic ring, either of which may be unsubstituted or substituted with lower alkyl, lower alkoxyalkyl or lower alkenyloxy, $R_{14}$ is O, S or NH, $R_{15}$, $R_{16}$ and $R_{17}$ are each independently hydrogen or lower alkyl, and r, s and t are independently 0 or 1 with either of the chiral selectors described above, said selector being an R or S enantiomer, under conditions effective to form a complex between an enantiomer of said first compound having said first optical configuration and the enantiomer of the chiral selector and recovering the noncomplexed enantiomer of said first compound having said second optical configuration.

DESCRIPTION OF THE PREFERRED EMBODIMENTS

Figure 1:
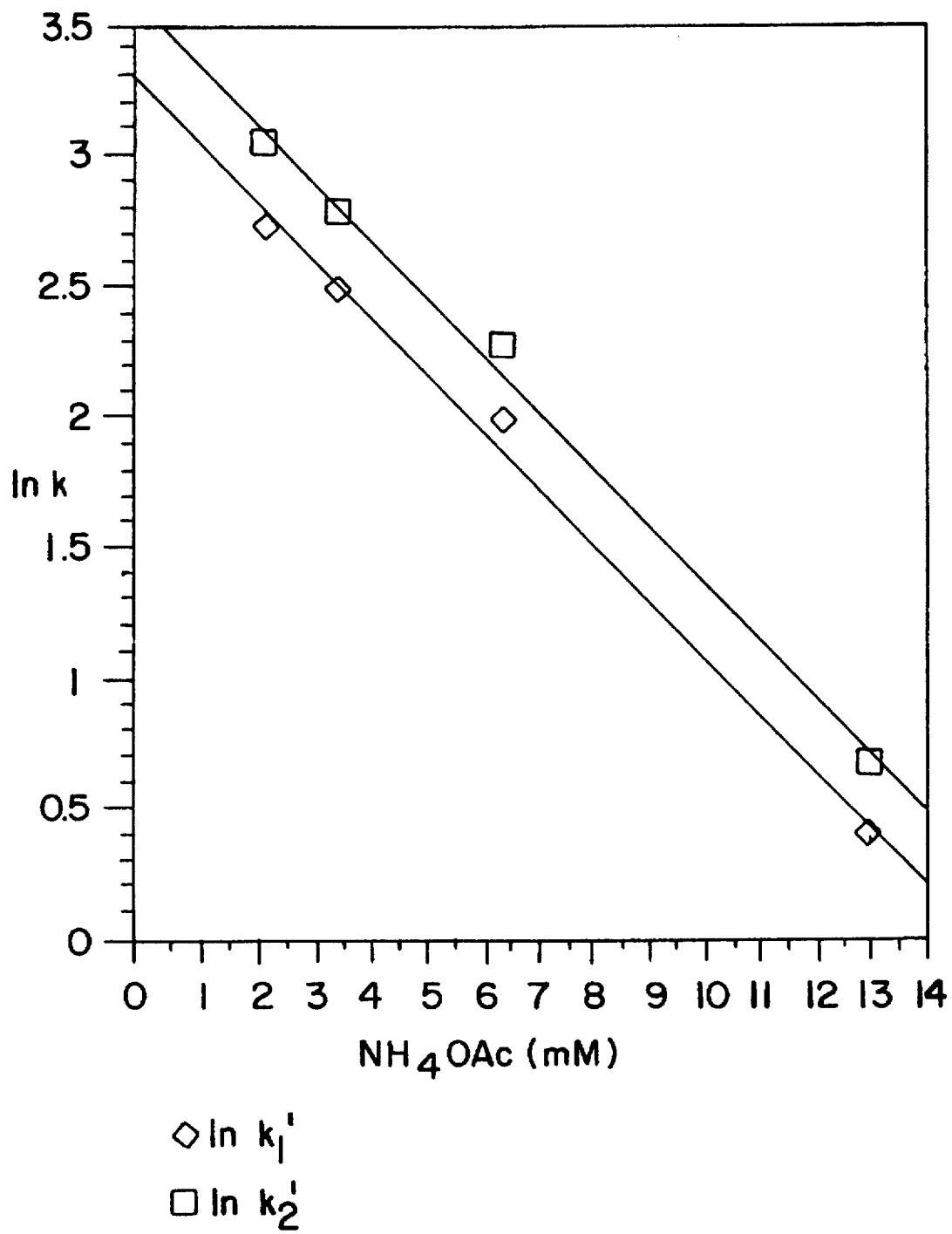
FIG. 1 is a graph of the relationship between the retention of enantiomers on a preferred chiral selector of the invention and the quantity of ammonium acetate in the mobile phase in an LC column.

The present invention relates to the separation of β-amino alcohol compounds, particularly compounds known as β-blockers, by employing what is known as a chiral selector compound which can achieve separation of enantiomers without requiring derivatization of the enantiomers before effecting separation.

The process of the invention concerns a separation of enantiomers of underivatized amino alcohol compounds. This class of compounds may be identified by the general formula:

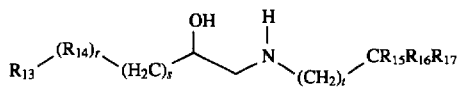

wherein

- $R_{13}$ is aryl or a nitrogen, sulfur or oxygen containing heterocyclic ring, either of which may be unsubstituted or substituted with lower alkyl, lower alkoxyalkyl or lower alkenyloxy,
- $R_{14}$ is O, S or NH,
- $R_{15}$, $R_{16}$ and $R_{17}$ are each independently hydrogen or lower alkyl, and
- r, s and t are independently 0 or 1.

These compounds are of the R or S optical configuration and when prepared are usually produced as the racemic modification. Hence, the necessity for achieving separation.

Among the preferred β-amino alcohol compounds, which may be separated by the process of the subject invention, are pharmaceutical compounds known as β-blockers. In one group of β-blockers as depicted by the general formula, $R_{14}$ is O, and r is 1, while in another similar group as depicted by the general formula, r is 0, thereby eliminating $R_{14}$ from the formula. The structures of commonly employed β-blockers are depicted in Table I, below:

like. The preferred alkoxy and the preferred alkyl groups each contain 1 to 3 carbon atoms.

The lower alkenyloxy groups, singly or in combination with other groups contain up to 6 carbon atoms which may be in the normal or branched configuration including, for example, ethenyloxy, propenyloxy, butenyloxy, pentenyloxy and hexenyloxy and the like. The preferred alkenyloxy groups contain 2 to 3 carbon atoms.

The aryl groups are aromatic rings containing from 6 to 10 ring carbon atoms. The aryl groups include phenyl, α-naphthyl and β-naphthyl. The aryl group is preferably phenyl.

As employed herein, the expression "nitrogen, sulfur or oxygen containing heterocyclic ring" is meant to include those heterocyclic rings which include at least one sulfur, nitrogen or oxygen ring atom but which may include one or several of said atoms. The expression also includes saturated, and unsaturated heterocyclics as well as the heteroaromatic rings. These groups contain from 5 to 10 ring atoms on the heterocyclic moiety. Representative heterocyclics include furan, thiphene, pyrrole, pyridine, pyrazole, pyrazine, pyrimidine, pyridazine, oxazole, quinoline, isoquino-

TABLE I

β-Blocker structures

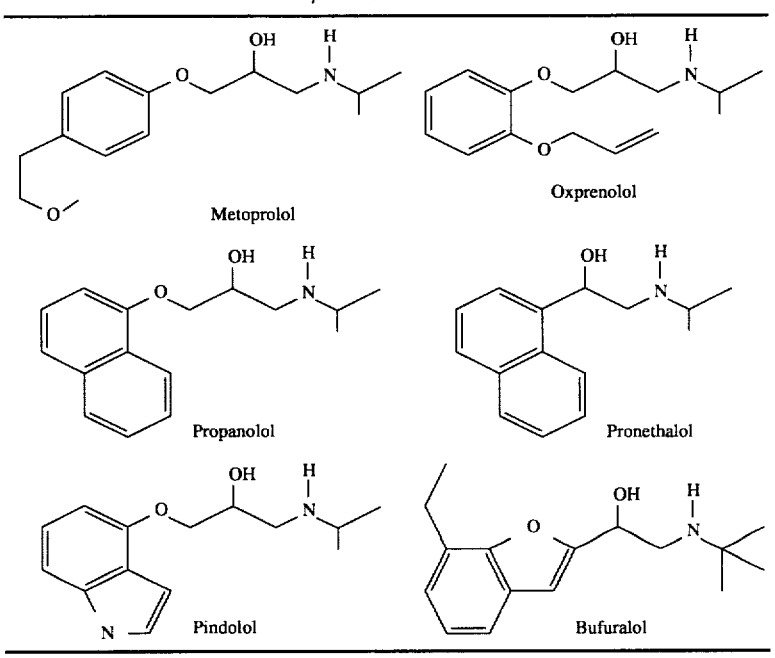

The substituents in the formulas herein are described as follows:

As employed herein, the lower alkyl groups, singly or in combination with other groups, contain up 5 to 6 carbon atoms which may be in the normal or branched configuration including methyl, ethyl, propyl, isopropyl, butyl, isobutyl, t-butyl, amyl, pentyl, hexyl and the like. The preferred alkyl groups contain 1 to 3 carbon atoms.

The lower alkoxyalkyl groups, singly or in combination with other groups, contain up to 12 carbon atoms with each alkoxy or alkyl group containing up to 6 carbon atoms which may be in the normal or branched configuration including for example, methoxymethyl, methoxyethyl, methoxypropyl, methoxyhexyl, ethoxymethyl, ethoxypropyl, propoxymethyl, propoxyhexyl, butoxyethyl, butoxypentyl, pentoxyethyl, pentoxyhexyl, hexoxyethyl, hexoxybutyl and the line, indole, benzothiophene, benzofuran, imidazole, benzoxazole, piperazine, tetrahydrofuran and the like. The preferred heterocyclics are indolyl, benzothienyl and benzofuranyl, especially 2- or 5-indolyl, 2- or 5-benzothienyl and 2- or 5-benzofuranyl.

The chiral selector of the first group of chiral selectors of the subject invention is a chemical compound having the following formula:

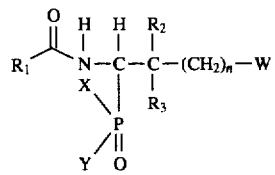

wherein $R_1$ is

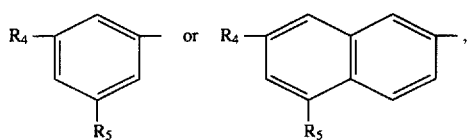

preferably
$R_1$ is

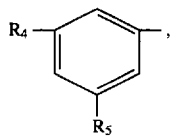

$R_2$ and $R_3$ are each independently lower alkyl, preferably methyl;

$R_4$ and $R_5$ are each independently $NO_2$, $N(R_6)_3^+$, $CN$, $COOR_7$, $SO_3H$ or $COR_8$, preferably $NO_2$;

$R_6$, $R_7$ and $R_8$ are each independently hydrogen or lower alkyl, preferably hydrogen or methyl, W is H or $CH=CH_2$, X and Y are each independently $OR_9$ or $NR_{10}R_{11}$, preferably X and Y are the same and most preferably X and Y are each $OR_9$, or X and Y together with the P to which they are attached form a 5- or 6-membered ring having the formula:

$$O=P-Z-CH \begin{matrix} R_{12} \\ | \\ | \end{matrix}$$
$$Z\!-\!-\!(CH_2)_m,$$

$R_9$, $R_{10}$, $R_{11}$ and $R_{12}$ are each independently hydrogen or lower alkyl, $R_9$ is preferably methyl, $R_{10}$, $R_{11}$ and $R_{12}$ are preferably hydrogen or methyl, Z is O or NH, n is 1 to 20, preferably 1 to 8 when W is H, and 1 to 3 when W is $CH=CH_2$, and m is 1 or 2, said compound being an R or an S enantiomer or a mixture of R and S enantiomers.

The preferred chiral selector of the first group of useful chiral selectors for effecting separation of β-amino alcohol compounds, particularly the β-blockers, is the chemical compound having the formula:

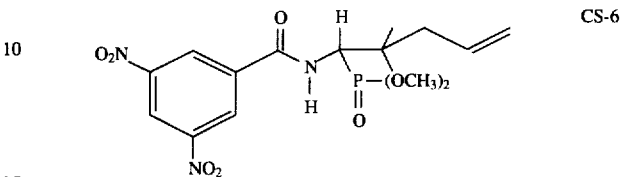

hereinafter identified as CS-6 and also known by its name, dimethyl N-(3,5-dinitrobenzoyl)-α-amino-2,2-dimethyl-4-pentenyl phosphonate.

The first group of chiral selectors of the invention may be prepared by conventional chemical preparative techniques. For illustrative purposes the preparation of the preferred chiral selector is described below, but one skilled in the art can readily appreciate the modifications necessary to prepare other chiral selectors within the scope of the chemical formula employed herein to depict the first group of useful chiral selectors.

The synthetic sequence used to prepare CS-6 is shown in Table II below.

TABLE II

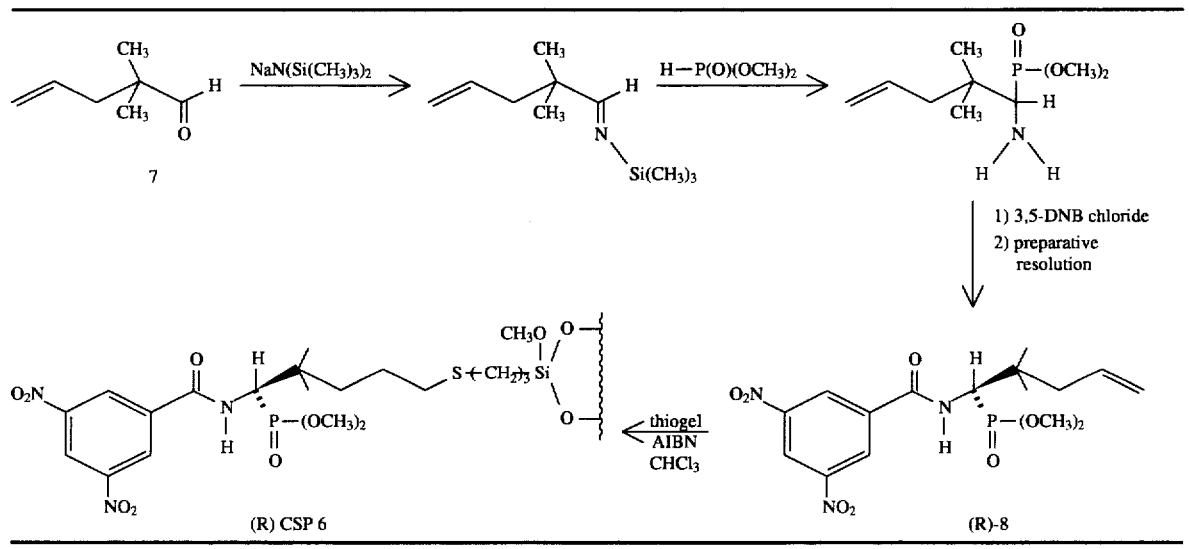

This preparation begins with an aldehyde, 4-pentenal, 2,2-dimethyl, readily available from the reaction of allyl alcohol and isobutyraldehyde. This aldehyde has a terminal double bond, which serves as a means for attachment to silica to form a CSP in a HPLC column, and is nonenolizable. Treatment of the aldehyde with sodium hexamethyldisilamide affords the N-trimethylsilyl imine which adds dimethyl phosphite to give, after workup, the α-amino phosphonate. The crude α-amino phosphonate is acylated with 3,5-dinitrobenzoyl chloride to afford the racemic precursor of CS-6, resolvable on a variety of known π-basic chiral stationary phases (CSPs). Preparative resolution of CS-6 can be accomplished using a large column containing a N-2-(naphthyl)alanine-based CSP. The enantiomerically pure phosphonate can be covalently bonded to 3-mercaptopropylsilanized silica using 2-2-azobis(2-methylpropionitrile) as an initiator. The modified silica gel is slurry packed into a 120×4.6 mm stainless steel column, endcapped with hexamethyldisilizane, and can then be evaluated for its ability to separate the enantiomers of an assortment of β-blockers and β-blocker analogs.

The chiral selector of the second group of chiral selectors of the subject invention is a β-lactam-derived chemical compound having the formula:

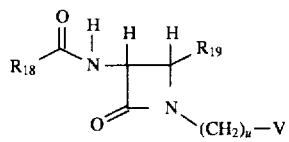
II wherein $R_{18}$ is

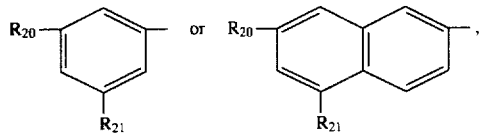

preferably $R_{18}$ is

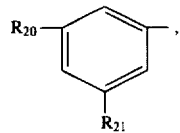

$R_{19}$ is lower alkyl or aryl, preferably t-butyl, phenyl or α-naphthyl, $R_{20}$ and $R_{21}$ are each independently $NO_2$, $N(R_{22})_3^+$, CH, $COOR_{23}$, $SO_3H$ or $COR_{24}$, preferably $NO_2$, $R_{22}$, $R_{23}$ and $R_{24}$ are each independently hydrogen or lower alkyl, preferably hydrogen or methyl, V is H or $CH=CH_2$, u is 1 to 20, preferably 1 to 11, said compound being an R or an S enantiomer or a mixture of R and S enantiomers.

The preferred chiral selector of the second group of useful chiral selectors for effecting separation of β-amino alcohol compounds, particularly the β-blockers, is the chemical compound having the formula:

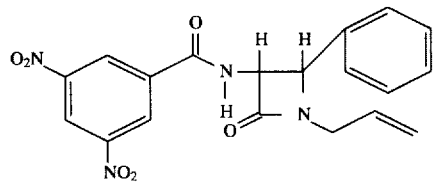
CS-7 hereinafter identified as CS-7 and also known by its name, cis-(N-3,5-dinitrobenzoyl)-3-amino-4-phenyl-1-prop-3-enyl-2-azetidinone.

The second group of chiral selectors of the invention may be prepared by conventional chemical preparative techniques. For illustrative purposes the preparation of the preferred chiral selector is described below, but one skilled in the art can readily appreciate the modifications necessary to prepare other chiral selectors within the scope of the chemical formula employed herein to depict the second group of useful chiral selectors.

The synthetic sequence used to prepare CS-7 is shown in Table III below.

TABLE III

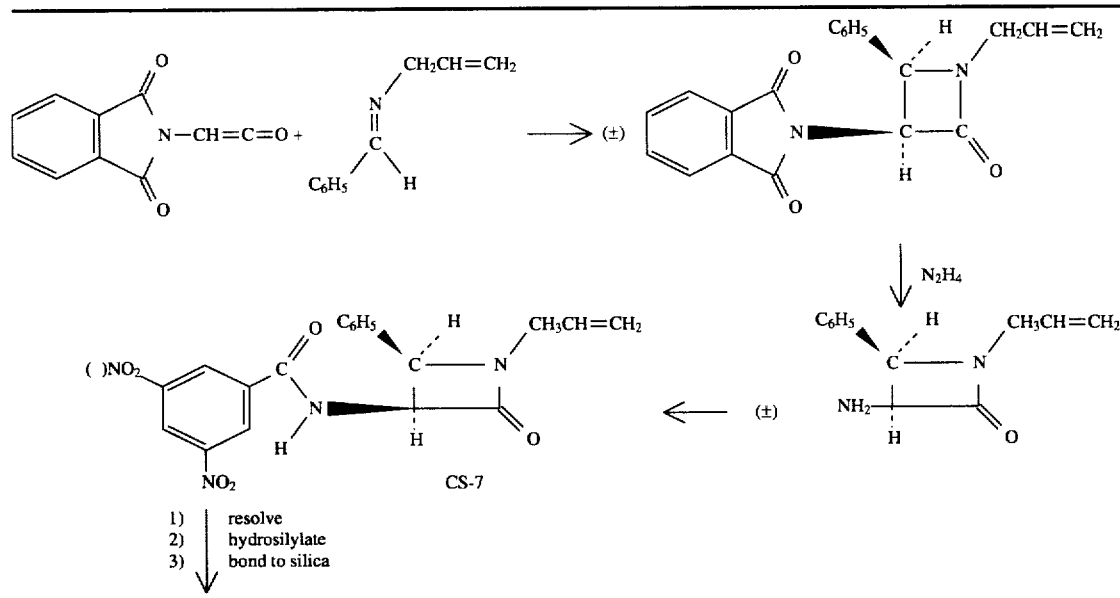

TABLE III-continued

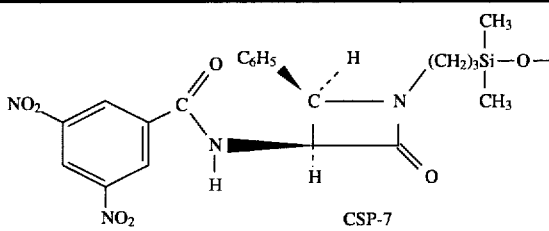

CSP-7

Owing to the widespread interest in the synthesis of α-amino β-lactams, a number of synthetic approaches to these compounds are known. The cycloaddition of a ketene to an imine is straightforward and offers the possibility for facile changes in the structure of the β-lactam. As shown in Table III, cycloaddition of the ketene derived from N-phthalimido glycine to an imine derived from an aldehyde and a terminally unsaturated alkenylamine affords, after removal of the phthalimido protecting group, a racemic α-amino β-lactam. As a rule, the cis-isomers are preferentially formed in these reactions. N-Acylation with 3,5-dinitrobenzoyl chloride, chromatographic separation of the enantiomers, hydrosilylation of the terminal double bond and bonding of the chiral organosilane to silica as described above when preparing the first group of chiral selectors completes the synthesis of the second group of chiral selectors.

Enantiomer separation by means of the chiral selectors of the invention may be achieved in a variety of techniques known in the art. In one embodiment the chiral selector may form the active portion of the stationary phase in a HPLC column as described above. Since the chiral selectors of the invention are optically active, it is necessary to separate the chiral selector so that either the R or the S enantiomer of the chiral selector is employed as part of the stationary phase in the column depending upon which of the enantiomers to be separated is to be preferentially bound to the chiral selector. In this embodiment the terminal W of the formula for the first group of chiral selectors or the terminal V of the formula for the second group of chiral selectors must be $CH=CH_2$ so as to permit the chiral selector to be immobilized on a support which is suitable for use in chromatographic applications. In one configuration the chiral selector is immobilized by covalently bonding it to silanized silica, such as, for example, γ-mercaptopropyl silanized silica.

The effect of temperature on the chromatographic behavior of β-blocker enantiomers is unusual. The reduction of temperature is found to reduce the retention of the least retained enantiomer when employing the chiral selectors of the invention, while increasing the retention of the more retained enantiomer without appreciable band broadening.

The techniques of enantiomer separation by HPLC are known in the art. Commercially available HPLC columns employing chiral stationary phases, such as those available from Regis Chemical Company can be employed in practicing the subject invention. See, for example, "Systematic Studies of Chiral Recognition Mechanisms," W. H. Pirkle, et al., Pages 23–35 in "Chiral Separations," Stephenson and Wilson, ed., Plenum Press, New York, 1988, the contents of which are incorporated herein by reference).

In another embodiment, the chiral selectors of the subject invention may be employed to effect separations employing semi-permeable membranes wherein the chiral selector forms part of a mobile phase. Such techniques are also well known employing semi-permeable membranes including those in the form of hollow fiber membranes. In this embodiment, it is preferred that the terminal W in the formula for the first group of chiral selectors or the terminal V of the formula for the second group of chiral selectors should be hydrogen to minimize covalent bonding by the chiral selector. In one particularly useful embodiment, the chiral selector forms part of a liquid membrane passing on one side of a semi-permeable barrier with the enantiomers to be separated passing on the other side of the barrier. The pores of the barrier become impregnated with the liquid membrane containing the chiral selector. One of the enantiomers complexes with the chiral selector, passes through the barrier into the moving liquid membrane and is conducted to a second location where disassociation takes place. This technique is disclosed in U.S. Pat. No. 5,080,795 to Pirkle et al., the contents of which are incorporated herein by reference.

EXAMPLES OF THE FIRST GROUP OF CHIRAL SEPARATORS

Apparatus

Chromatography was performed using either of two systems: system one consists of an Anspec-Bischoff model 2200 isocratic HPLC pump, a Beckman 210 injector with 20 μL sample loop, a Milton Roy LDC uv Monitor $D^R$ fixed wavelength detector operating at 254 nm, and a Kipp and Zonen BD 41 Dual channel recorder. A Rudolph Autopol III with a 20-cm flow cell was used to monitor the sign of [α]D. System two consists of an Anspec-Bischoff model 2200 isocratic HPLC pump, a Rheodyne 7125 injector with 20 μL sample loop, two Milton Roy LDC uv Monitor $D^R$ fixed wavelength detectors connected in series operating at 254 nm and 280 nm and a Kipp and Zonen BD 41 Dual channel recorder.

The allyl alcohol, isobutyraldehyde and dimethyl phosphite were purchased from Aldrich Chemical Company and distilled prior to use. The 2-acetylbenzofuran was used as received from Aldrich Chemical Company. DNB PG is available from Regis Chemical Company as is the N-(2-naphthyl)alanine undecyl ester CSP.

Preparation of Dimethyl N-(3,5-dinitrobenzoyl)-α-amino 2,2-dimethyl-4-pentenyl phosphonate (CS-6) (See Table II, supra.)

A 100 ml oven dried flask was charged with 2.20 g (12 mmol) of sodium hexamethyldisilamide and 50 ml of dry THF followed by 1.75 g (12 mmol) of aldehyde, 4-pentenal, 2,2-dimethyl, and magnetically stirred under a $N_2$ atmosphere at room temperature. After 1 hour, dimethyl phosphite 2.50 g (22.7 mmol) was added and the cloudy mixture brought to reflux for 24 hours. After cooling, the reaction mixture was diluted with 200 ml of $Et_2O$, followed by 100 ml of saturated $NaHCO_3$, the resulting mixture was stirred for 1 hour, the phases were separated and the organic layer was washed with 50 ml $H_2O$ then 50 ml of saturated NaCl. The combined aqueous layers were back extracted with three 50 ml portions of $CH_2Cl_2$. The combined organic layers were dried over $Na_2CO_3$. After filtration, the solution of crude amino phosphonate was treated with 3.51 g (15 mmol) of 3,5-dinitrobenzoyl chloride and 100 ml of 1:1 $H_2O$ and saturated NaHCO$_3$. After stirring for one hour, the aqueous layer was removed and replaced with 100 ml of 1:1 H$_2$O and saturated NaHCO$_3$. After stirring for an additional hour, the layers were separated and the organic layer was washed with 50 ml of saturated NaCl, dried over MgSO$_4$ and concentrated under reduced pressure. After column chromatography on silica using 2:1 CH$_2$Cl$_2$:Et$_2$O as eluent, (±) CS-6 was obtained as a colorless oil (1.35 g 25% yield). TLC R$_f$=0.30 (Silica/1:1 CH$_2$Cl$_2$:Et$_2$O). $^1$H NMR (C$^2$HCl$_3$) δ1.15 two s 6H; 2.24 m 1H; 2.32 m 1H; 3.75 d (J=16 Hz) 3H; 3.80 d (J=16 Hz) 3H; 4.6–4.92 dd J=20, 10 Hz) 1H; 5.20 m 2H; 5.90 m 1H;7.4 d (J=10 Hz) 1H; 9.02 m 2H; 9.19 m 1H. $^{31}$P{$_1$H} NMR (C$^2$HCl$_3$) δ25.78 (ref 85% H$_3$PO$_4$). IR (KBr, neat) 3248, 3098, 2961, 1734, 1670, 1630, 1541, 1344, 1284, 1234, 1035 cm$^{-1}$. mass spectrum (70 eV) 415 (0.8); 238 (18.0); 195 (100); 149 (82.5); 75 (76.7). high resolution mass spectrum, calculated for C$_{16}$H$_{22}$N$_3$O$_8$P: 415.1144. Found: 415.1137.

Resolution of racemic CS-6

Enantiomer separation was accomplished by medium pressure liquid chromatography on a 1×30 in. column packed with (+)-(R)-N-(2-naphthyl)-alanine undecyl ester CSP bonded to 60 um irregular silica. The mobil phase was 2% isopropyl alcohol in hexane. Two chromatographic fractions were collected. The first was (+)-(R)-CS-6 of 98% enantiomeric purity, as judged by HPLC assay on a Regis (R)-N-(2-naphthyl)-alanine column. The subsequently collected (−)-(S)-CS-6 was found to be of 99% enantiomeric purity. Each enantiomer was obtained as a colorless foam after drying in vacuo. The NMR spectrum of each enantiomer was identical to that of the racemate.

Chiral stationary phase of CS-6

Mercaptopropyl silica, 2.75 g, 0.60 g of enantiomerically pure (R)-CS-6 and 0.10 g of 2,2'-azobis(2-methylpropionitrile) were slurried in 30 mL of CHCl$_3$ and brought to reflux. After 36 h, the light red mixture was cooled and the derivatized silica was collected by filtration. The silica was washed sequentially with 100 mL of methanol, 50 mL of ethyl acetate, and 50 mL of diethyl ether. The modified silica was packed as a methanol slurry into a 120×4.6 mm I.D. column using conventional methods. Found: C, 5.80%; H, 1.03%; N, 0.69%. Calculated: 0.15 mmol/g (based on C ); 0.16 mmol/g (based on N).

Analytes and their separation

The β-blockers samples were provided by pharmaceutical companies. Pindolol from Sandoz, Ltd., Basle, Switzerland. Metoprolol from Ayerst Laboratories, Inc. Proenthalol and Propranolol from Imperial Chemical Industries. Oxprenolol from Ciba-Giegy. Bufuralol and its methylated analogs were provided by Roche Products Limited.

Since the presence of a basic amino group in an analyte typically leads to long retention and peak tailing on silica-based π-acidic CSPs, control of mobile phase pH and/or addition of amines to the mobile phase are frequently used cures for such peak tailing. Mobile phases consisting of halocarbons and lower molecular weight molecular alcohols and containing a low concentration of ammonium acetate have permitted separation of enantiomers of propranolol on known CSPs. The ammonium acetate provides a means of protonating the amino group of the β-blockers and reduces peak tailing. Increasing the concentration of the ammonium acetate in the mobile phase diminished retention of propanolol on CS-6, but: did not drastically alter enantioselectivity, thus suggesting that the ammonium acetate competes with the protonated β-blockers for absorption sites. This behavior is shown in FIG. 1 using a chloroform-methanol mobile phase. In the case of preparative separations, the volatility of the mobile phase components including ammonium acetate makes it possible to retrieve the β-blocker simply by evaporation of the mobile phase under vacuum.

Enantiomeric mixtures of the β-blockers of interest and some of their analogs were subjected to separation with HPLC columns to compare the effectiveness of prior art chiral separators and CS-6 of the invention when forming the active part of the stationary phase in the column.

A mobile phase of 19:1 dichloromethane-ethanol containing 0.5 g/L (6.5 mM) of ammonium acetate was used. To improve reproducibility, a stock solution of ammonium acetate in absolute ethanol was prepared and diluted with dichloro-methane as required. Comparative chromatographic data for six β-blockers were obtained using (R)-CSP-6 of the invention and two known CSPs, a commercial covalent (R)-N-(3,5-dinitrobenzoyl)phenylglycine derived phase (DNB PG), and (R)-dimethyl N-(3,5-dinitrobenzoyl)-α-amino-4(3-propenyl-1-oxy) benzyl phosphonate (CSP-5). The results are presented in Table IV.

TABLE IV

Separation of the Enantismers of Some β-Blockers

| Analyte | (R) DNB PG | | | (R) CSP 5 | | | (R) CSP 6 | | |
|---|---|---|---|---|---|---|---|---|---|
| | α$^a$ | k$_1$$^b$ | [α]$_D$$^c$ | α$^a$ | k$_1$$^b$ | [α]$_D$$^c$ | α$^a$ | k$_1$$^b$ | [α]$_D$$^c$ |
| Metoprolol | 1.05 | 9.86 | | 1.15 | 6.57 | | 1.16 | 2.57 | |
| Oxprenolol | 1.00 | 16.10 | | 1.00 | 6.14 | | 1.00 | 2.28 | |
| Pronethalol | 1.03 | 11.20 | | 1.06 | 12.36 | | 1.13 | 5.14 | |
| Propranolol | 1.00 | 12.80 | | 1.34 | 13.40 | (+)R | 1.39 | 4.36 | (+)R |
| Pindolol | 1.12 | 45.10 | | 1.12 | 50.10 | | 1.30 | 15.00 | |
| Bufuralol | 1.16 | 4.94 | (+)R | 1.22 | 6.67 | (+)R | 1.93 | 2.79 | (+)R |

$^a$Chromatographic separation factor
$^b$The capacity factor for the first eluted enantiomer using 19:1 CH$_2$Cl$_2$:CH$_2$CH$_2$OH with 0.5 grams/liter NH$_4$O$_2$CCH$_3$ as the mobile phase, flow rate of 2 mL per minute. The detector was operating at 254 nm.
$^c$Sign of [α]$_D$ of the more strongly retained enantiomer as determined by a polarimetric HPLC detector. The letter refers to the absolute configuration of the more strongly retained enantiomer.

From these data, it is evident that the more π-basic B-blockers are the more strongly retained. However, enantioselectivity does not necessarily parallel retention. Note that bufuralol is one of the more weakly retained, judged by k$_1$', of the β-blockers on CS-6, yet affords the largest separation factor in the table.

Figure 2A:
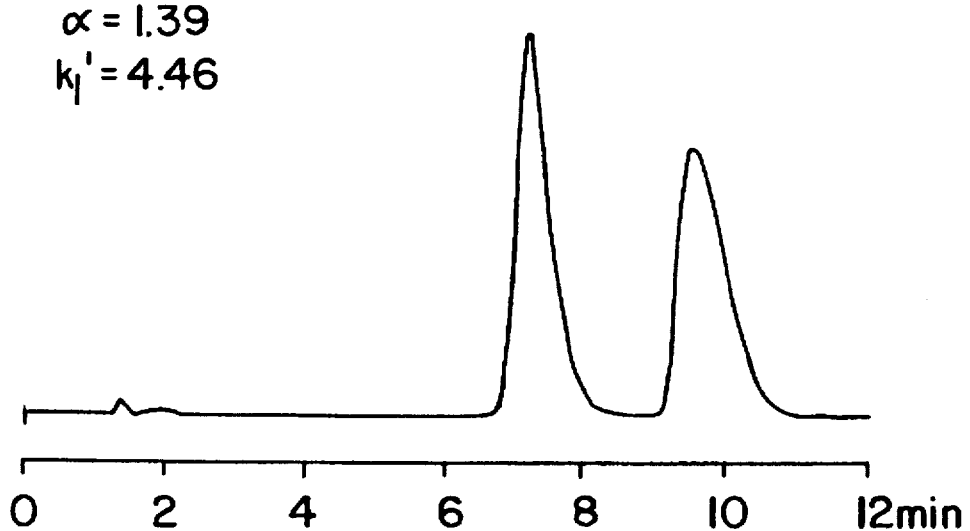
FIGS. 2a–2c are is a plots showing the effect of temperature and enantioselectivity on a preferred chiral selector of the invention.
Figure 2B:
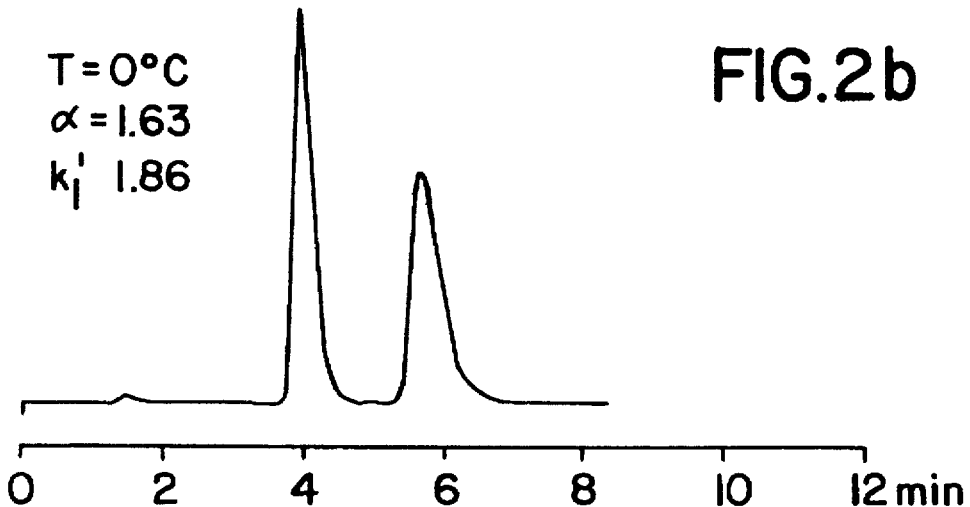
Figure 2C:
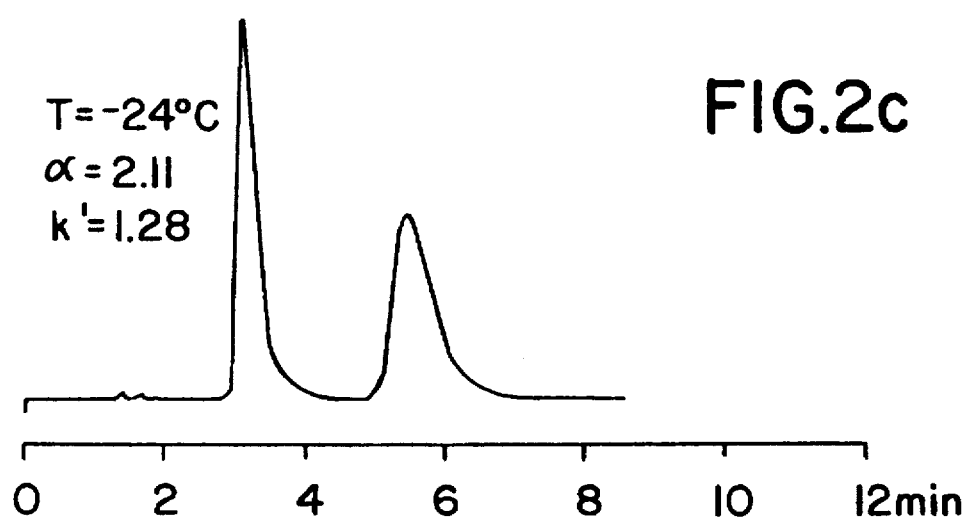
Figure 3A:
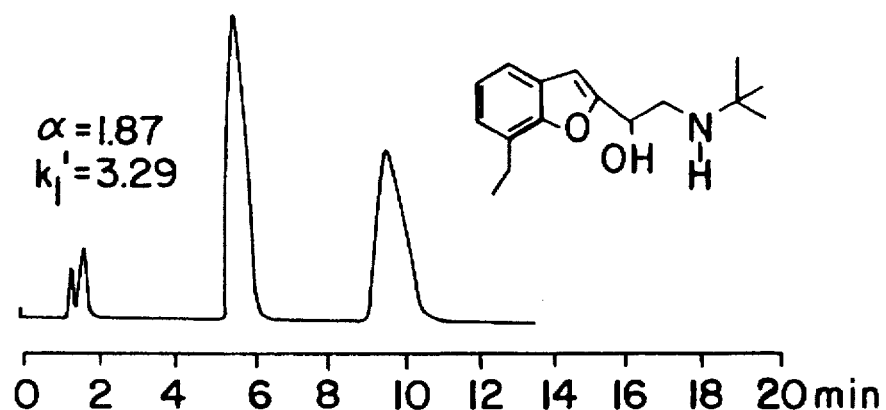
FIGS. 3a–3c are is a plot showing the influence on ring methylation on the retention and enantioselectivity of several analogs on a preferred chiral selector.
Figure 3B:
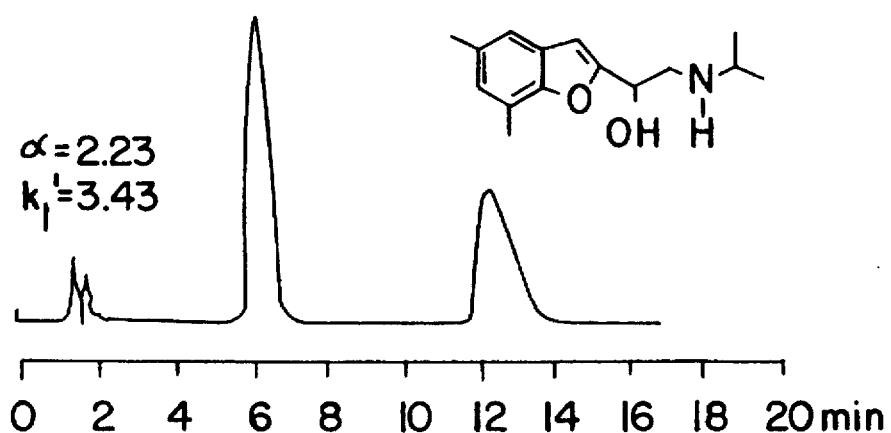
Figure 3C:
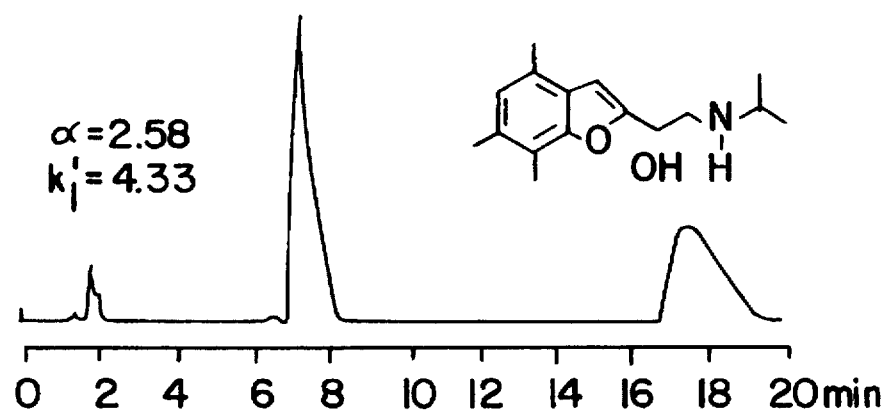

The elution orders on CSP-5 and CS-6 can be explained although this may not be in accord with the elution order noted on (R)-DNB PG. Owing to the Cahn-Ingold-Prelog priority sequence, (R)-CSP-5 and (R)-CS-6 are stereochemically equivalent to (S)-DNB PG. To further evaluate the chiral recognition process, the effect of temperature on β-blocker retention by CSP-5 and CS-6 was investigated. A linear van't Hoff response (i.e., a linear ln k' versus 1/T plot) is generally expected with increases in retention, enantioselectivity and peak width as the column temperature is reduced. Using the CSP-mobile phase combination described, nonlinear van't Hoff behavior was observed for an extended series of β-blockers and their analogs. As can be seen from the data in Table V, there are dramatic increases in enantioselectivity with comparatively little accompanying peak broadening (see FIGS. 2a–2c). In view of the number of equilibria possible in these rather complex systems, equilibria which may respond differently to temperature change, no rationalization of these observations can be offered.

quently, it is more restricted conformationally, a circumstance often associated with appreciable degrees of enantioselectivity. Note that replacing the 7-ethyl substituent of bufuralol with two, or better, three, methyl substituents on the benzofuran ring enhances enantioselectivity by increasing the π-basicity without adding polar sites for additional bonding interactions with the stationary phase (see FIGS. 3a–3c) which increase retention but may possibly reduce enantioselectivity. The methyl substituents enhance enantioselectivity relative to bufuralol even though the analogs have N-isopropyl substituents, shown herein to be inferior to N-t-butyl substituents in engendering enantioselectivity in bufuralol-like systems. For example, a series of bufuralol-

TABLE V

The Effect of Temperature Upon Retention and Enantioselectivity for Some of β-Blockers and Analogs using CS 6

| Analyte | 21° C. | | 0° C. | | −24° C. | |
|---|---|---|---|---|---|---|
| | $\alpha^a$ | $k_1^b$ | $\alpha^a$ | $k_1^b$ | $\alpha^a$ | $k_1^b$ |
| metoprolol | 1.16 | 2.57 | 1.21 | 1.05 | 1.48 | 0.64 |
| oxprenolol | 1.00 | 2.28 | 1.00 | 0.75 | 1.03 | 0.50 |
| pronethalol | 1.13 | 5.14 | 1.21 | 2.21 | 1.31 | 1.50 |
| propranolol | 1.39 | 4.46 | 1.63 | 1.86 | 2.11 | 1.28 |
| pindolol | 1.30 | 15.0 | 1.43 | 7.29 | 1.72 | 6.71 |
| bufuralol | 1.93 | 2.79 | 2.50 | 1.43 | 4.08 | 0.73 |
| [structure] | 2.15 | 3.43 | 2.83 | 2.07 | 4.18 | 1.57 |
| [structure] | 2.23 | 3.28 | 3.04 | 1.86 | 4.44 | 1.46 |
| [structure] | 2.58 | 4.43 | 3.44 | 2.57 | 5.03 | 2.21 |
| [structure] | 1.75 | 4.14 | 2.38 | 1.86 | 3.76 | 1.13 |
| [structure] | 1.64 | 4.01 | 2.08 | 1.80 | 3.08 | 1.08 |
| [structure] | 1.63 | 1.71 | 1.94 | 1.19 | 3.02 | 0.73 |

<sup>a</sup>Chromatographic separation factor
<sup>b</sup>The capacity factor for the first eluted enantiomer using 19:1 $CH_2Cl_2$:$CH_3CH_2OH$ with 0.5 grams/liter $NH_4O_2CCH_3$ as the mobile phase, flow rate of 2 mL per minute. The detector was operating at 254 nm.

Figure 4:
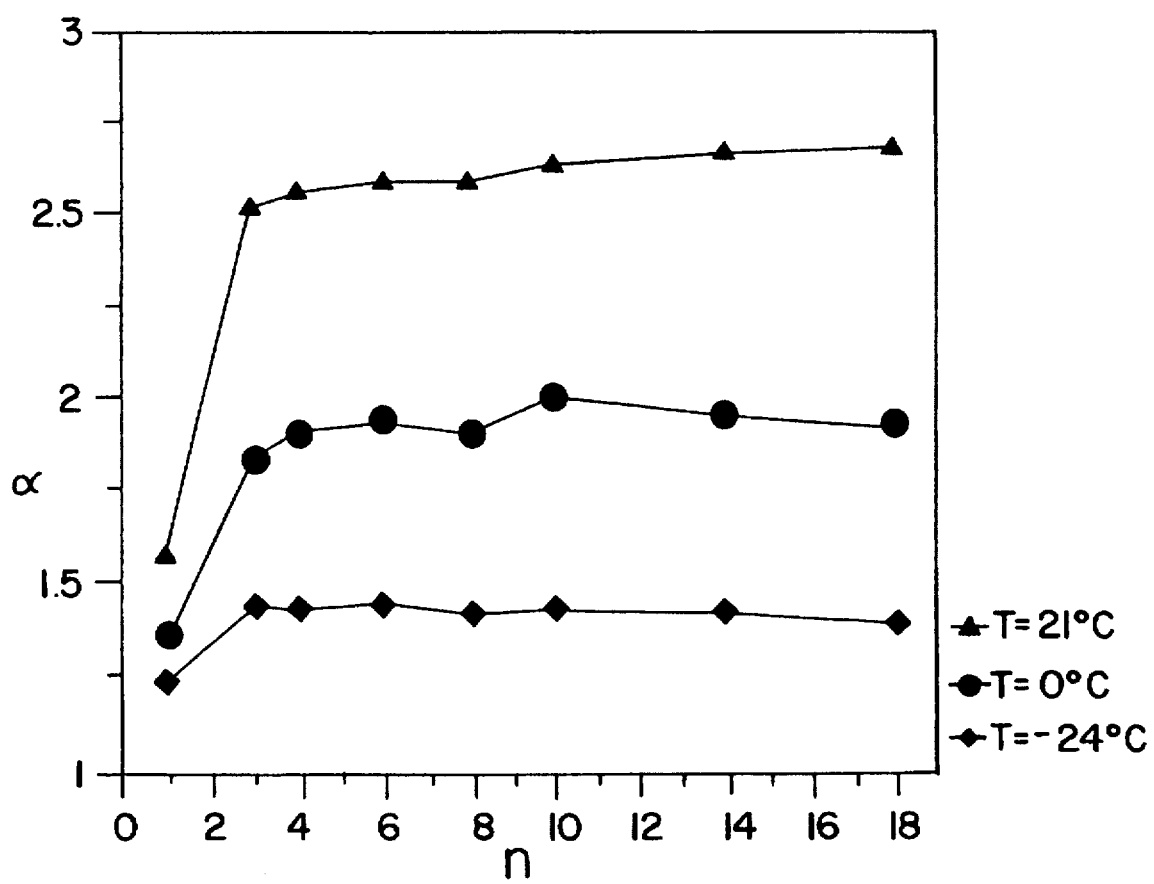
FIG. 4 is a graph showing the relationship between enantioselectivity on a preferred chiral selector of the invention and the number of methylenes in the N-alkyl substituent on a particular β-amino alcohol compound at three temperatures.
Figure 4:
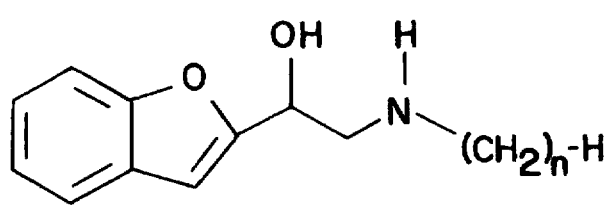

It was not surprising that the enantiomers of bufuralol were better resolved than those of propranolol. Unlike the latter two, bufuralol lacks the methylene group between the π-basic aromatic group and the stereogenic center. Conselike racemates was prepared by a synthetic route which allows variation of the N-alkyl substituent (see Table VI, below). This sequence, similar to that reported for bufuralol, entails α-bromination of 2-acetylbenzofuran, reduction of the bromo ketone to the bromo alcohol with sodium borohydride, and the substitution of the desired n-alkylamine for the bromine. FIG. 4 shows the effect of the length of the N-alkyl substituent upon α at 21° C., 0° C., and −24° C. As may be seen, alkyl groups longer than propyl have negligible effect upon the magnitude of α, suggesting that the enantiomers show either no or little differential intercalation of the N-alkyl groups between strands of bonded phase.

TABLE VI

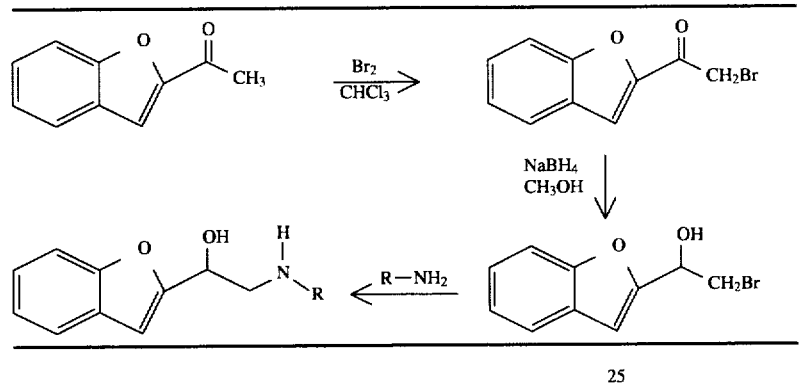

Figure 5:
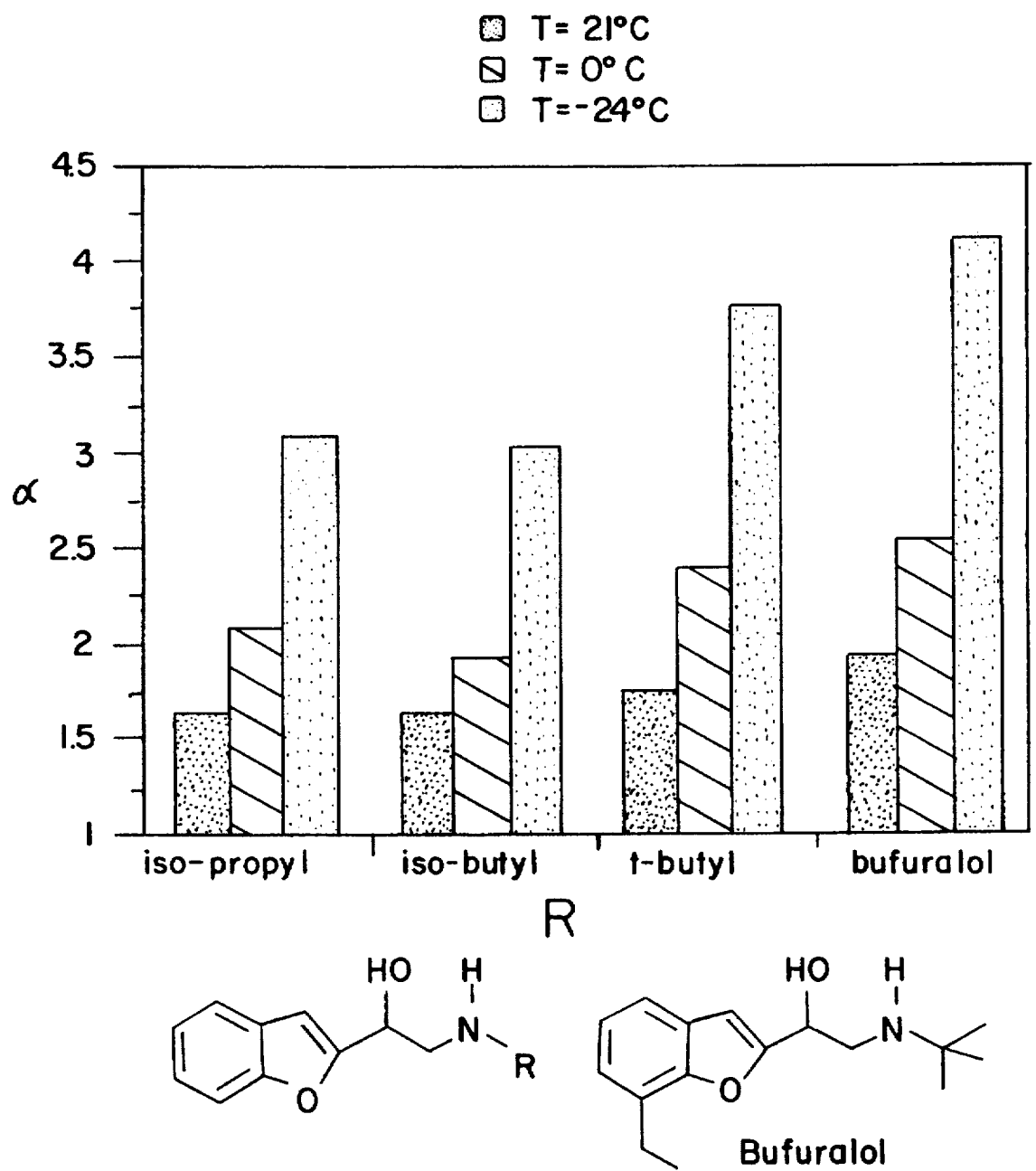
FIG. 5 is a graph showing the relationships between enantioselectivity on a preferred chiral selector of the invention and the alkyl substituent on the nitrogen of a particular β-amino alcohol compound at three temperatures.

In all instances, α increases dramatically as the temperature is diminished. Chromatographic response to temperature change of the bufuralol analogs having N-isopropyl, N-isobutyl and N-t-butyl substituents is shown in Table V. The N-isopropyl and N-isobutyl analogs show comparable levels of enantioselectivity at ambient temperature and are exceeded in this respect by the N-t-butyl analog. This difference is accentuated at lower temperatures. All three analogs show lower selectivities than bufuralol, doubtless owing to the absence of a π-basicity-enhancing alkyl substituent on the benzofuran system. FIG. 5 shows this relationship between α and the alkyl group on the nitrogen of bufuralol analogs at three temperatures when CS-6 is the chiral selector.

Elution orders were rigorously established using β-blocker samples of known absolute configuration. In some instances, the signs of the rotation of the enantiomers were related to elution orders using a polarimetric detector in series with the ultraviolet detectors. The observed elution orders on CSP-5 and CS-6 are consistent with the a priori formulated chiral recognition model, such as that of Table VII below, as are the structure-activity relationships noted. It is evident that the first group of chiral selectors of the invention, particularly CS-6, are useful for both analytical and preparative scale separations of a variety of β-blockers, no derivatization being required.

TABLE VII

Chiral Recognition model

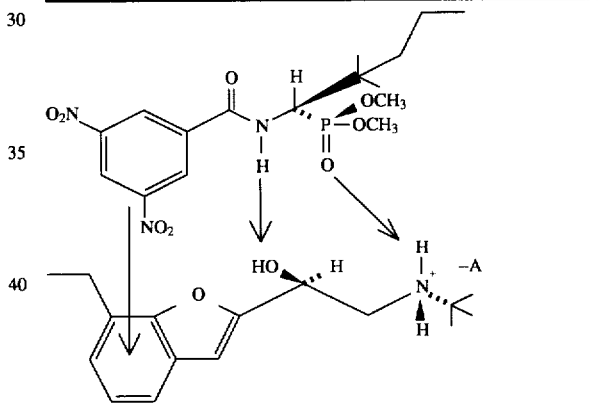

EXAMPLES OF THE SECOND GROUP OF CHIRAL SEPARATORS

Apparatus

High performance liquid chromatography (HPLC) experiments were performed using a Rainin HPX solvent delivery system and pressure monitor, a Rheodyne 7125 injector with a 20 ul sample loop, a Milton Roy LDC Monitor D fixed wavelength detector operating at 254 nm and a Kipp and Zonen BD 41 recorder. All reactions were performed under a nitrogen atmosphere, unless otherwise noted. The $^1$H NMR spectra were obtained on a Varian XL-200. All $^1$H resonances are reported relative to internal tetramethylsilane. Infrared spectra were obtained on an IBM IR 32 FT-IR. Low resolution mass spectra were obtained on a Varian MAT CH-5 mass spectrometer with 70eV electron impact ionization. High resolution mass spectra were obtained on a Varian 731 mass spectrometer with 70eV electron impact ionization. Melting points were taken using a Buchi melting point apparatus in open capillary tubes and are uncorrected. All reagents used were of reagent grade. Dry dichloromethane was freshly distilled from $CaH_2$ under nitrogen prior to use. The various analytes used in this study were available from prior studies.

Preparation of cis-4-phenyl-3-phthalimido-1-prop-3-enyl-2-azetidinone ( See Table III)

Allyl amine 5.5 mL ( 73.3 mmol ) was placed with 30 g dried molecular sieve (4Å) in the oven, 120mL dry $CH_2Cl_2$ and cooled to 0° C. The distilled benzaldehyde 13.1 mL (30.5 mmol) was added dropwise and the mixture was stirred for 4.5 hr at room temperature. The reaction mixture was evaporated to remove excess amine under the reduced pressure. The residue oil was diluted with 100 ml of dry $CH_2Cl_2$ with triethylamine 5.1 mL (36.6 mmol). 6.73 g (30.1 mmol) of phthalimidylacetyl chloride in 50 ml of dry $CH_2Cl_2$ was dropwise added to the reaction mixture in an ice-bath and stirred for 20hr at room temperature. After the molecular wieve was filtered, the reaction mixture was washed with 150 mL of 1N NaOH and 150 mL of brine, respectively. The organic layer was dried over $MgSO_4$ and concentrated in vacuo. The crude mixture was purified with chromatography over silica gel to obtain pure 2.9 g of cis-2-phthalimido-β-lactam. $^1H$ NMR ($CDCl_3$) δ:3.77 (dd, J=15.2 and 7.0 Hz, 1H), 4.43 (dd, J=15.4 and 5.2 Hz, 1H), 5.37 (d, J=5.6 Hz, 1H), 5.21–5.30 (m, 2H), 5.54 (d, J=5.6 Hz, 1H), 5.80–6.00 (m, 1H), 7.1–7.3 (m, 5H), 7.6–7.75 (m, 4H); MP 181.5°–182.5° C.; Mass spectrum: m/z (relative intensity) 332 (2.8), 249 (58.0), 185 (99.5), 146 (100), 104 (67.6); Anal. Calcd for $C_{20}H_{16}N_2O_3$: C, 72.28: H, 4.85: N, 8.43; Found: C, 72.10: H, 4.82: N, 8.39; High-resolution mass spectrum: calculated for $C_{20}H_{16}N_2O_3$: 332.1161. Found: 332.1158.

Preparation of cis-(N-3,5-dinitrobenzoyl)-3-amino-4-phenyl-1-prop-3-enyl-2-azetidinone (CS-7, See Table III)

The cis-3-phthalimido-β-lactam (2.90 g, 8.7 mmol) was suspended in 10 ml of ethanol and 9.5 ml of a 1M solution of hydrazine hydrate in 95% ethanol was added. After refluxing for 6.5hr, the solvent was evaporated, diluted with methylene chloride. After the organic layer was acidified with 50 mL of 1N HCl, it was washed with methylene chloride, basified with 3N NaOH, extracted with methylene chloride (60 mL×3), washed with brine and dried with $MgSO_4$. After removal of solvent in vacuo, the crude product was used for the next step without further purification, cis-3-amino-4-phenyl-1-prop-3-enyl-2-azetidinone; $_1H$ NMR ($CDCl_3$) δ:116 (br.s, 2H), 3.47 (dd, J=15.5 and 7.0 Hz, 1H), 4.24 (dd, J=15.3 and 5.1 Hz, 1H), 4.48 (d, J=5.2 Hz, 1H), 4.84 (d, J=5.0 Hz, 1H), 5.07–5.18 (m, 2H), 5.65–5.85 (m, 1H), 7.20–7.48 (m, 5H); IR (neat, $cm^{-1}$) 3389, 3326, 1750, 930, 739. The dissolved 3,5-dinitrobenzoyl chloride 3.1 g (13.3 mmol) with 35 mL of dry $CH_2Cl_2$ was added to the above 3-amino-4-phenyl-β-lactam 1.43 g (7.1 mmol) and the triethylamine 2.0 mL (14.3 mmol) with 20 mL of dry $CH_2Cl_2$ in an ice-bath. The reaction mixture was stirred at room temperature for 1h, washed with 50 mL of 1N HCl, 2N NaOH solution (40 mL×2) and brine. The organic layer was dried over $MgSO_4$ and concentrated under reduced pressure. The corresponding product was chromatographed on silica gel. $^1H$ NMR ($CDCl_3$) δ: 3.68 (dd, J=15.6 and 7.0 Hz, 1H), 4.28 (dd, J=15.1 and 4.9 Hz, 1H), 5.16 (d, J=4.2 Hz, 1H), 5.20–5.31 (m, 2H) 5.63 (dd, J=7.2 and 4.4 Hz, 1H), 5.76–5.96 (m, 1H), 7.25–7.50 (m, 5H), 8.76 (d, J=2.4 Hz, 2H), 9.03–9.11 (m, 2H); Mass spectrum: m/z (relative intensity) 396 (0.2), 313 (49.9), 185 (63.4), 146 (100.0), 42 (43.8); Anal. Calcd for $C_{19}H_{16}N_4O_6$: C, 57.58: H, 4.07: N, 14.14; Found: C, 57.41: H, 4.02: N, 14.00: High-resolution mass spectrum: calculated for $C_{19}H_{16}N_4O_6$:396.1070. Found: 396.1069.

Resolution of the Racemic cis-(N-3,5-dinitrobenzotl)-3-amino-4,-phenyl-1-prop-3-enyl-2-azetidinone Enantiomerically pure sample was obtained by preparative medium pressure liquid chromatography on a 1"×30" column containing a (S)-N-(1-naphthyl)leucine derived CSP bonded to 60 µm irregular silica. The mobile phase was 20% (v/v) 2-propanol in hexane, and the flow rate was about 30 mL/min. The (+)-(3S, 4R)-cis-(N-3,5-dinitrobenzoyl)-3-amino-4-phenyl-1-prop-3-enyl-2-azetidinone enantiomer elutes second, the enantiomeric purity being >99% by an analytical column packed with the (S)-N-(1-naphthyl)leucine-derived CSP bonded to 5 µm regular silica. The (+)-(3S, 4R)-(N-3,5-dinitrobenzoyl)-3-amino-4-phenyl-1-prop-3-enyl-2-azetidinone [α]D=+33.57 (c 3.61 in $CH_2Cl_2$).

Preparation of (+)-(3S, 4R)-4-(11-Triethoxysilylpropyl)-(N-3,5-dinitrobenzoyl)-3-amino-4-phenyl-2-azetidinone (see Table III)

To a stirred solution of (+)-(3S, 4R)-resolved product (787 mg) in 20 ml of trichlorosilane with 5 ml of $CH_2Cl_2$ under a nitrogen atmosphere was added 57 mg of hexachloroplatinic acid. The resulting solution was heated to reflux for 6 hours. The excess trichlorosilane was removed by distillation at atmospheric pressure, methylene chloride was added as a chase and then removed by distillation. The residue was quenched with 6ml of 1:1 (v/v) absolute ethanol-dry triethylamine and concentrated under reduced pressure. The residue was purified on silica gel to afford 344 mg of the hydrosilylated product which is bonded directly to silica. $^1H$ NMR ($CDCl_3$) δ:0.68 (t, J=7.3 Hz, 2H), 1.21 (t, J=7.4 Hz, 9H), 1.77 (t, J=7.3 Hz, 2H), 3.09–3.25 (m, 1H), 3.62–3.78 (m, 1H), 3.82 (q, J=7.0 Hz, 6H), 5.16 (d, J=4.4 Hz, 1H), 5.58 (dd, J=7.4 and 4.8 Hz, 1H), 7.28–7.40 (m, 5H), 8.77 (d, J=1.8 Hz, 2H), 9.03–9.05 (m, 1H), 9.20 (d, J=7.4 Hz, 1H).

Preparation of Chiral Stationary Phase of (+)-(3S, 4R)-4-(11-triethoxysilylpropyl)-(N-3,5-dinitrobenzoyl)-3-amino-4-phenyl-2-azetidinone (CSP-6, See Table III)

Water was azeotropically removed from a slurry of 4.2 g 5 µm Rexchrom silica in 60 mL of benzene. After drying was complete, 344 mg of hydrosilylated product was dissolved in 30 mL of methylene chloride and added to the slurry. The solvents were evaporated under reduced pressure and the resulting slurry was mechanically rocked under reduced pressure at 80° C. for 30hr. The modified silica was washed with three 100 mL portions of methanol then slurry packed into a 4.6×250 mm column by conventional methods.

Found: C, 3.98%: H, 0.58%: N, 0.59% Calculated: 0.16 mmol/g (based on C): 0.26 mmol/g (based on H): 0.11 mmol/g (based on N).

Two other β-lactam-derived CS-8 and CS-9 were prepared in a manner similar to the preparation of CS-7. The relationship of CS-7, CS-8 and CS-9 are shown in Table VIII below, which set forth the individual substituents for each of the chiral selectors of the second group of chiral selectors of the subject invention.

TABLE VIII

| | $R_{18}$ | $R_{19}$ | u | V |
|---|---|---|---|---|
| CS-7 | 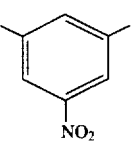 3,5-dinitrophenyl | 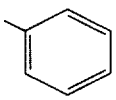 phenyl | 1 | $-CH=CH_2$ |
| CS-8 | 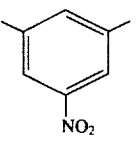 3,5-dinitrophenyl | t-butyl | 11 | $-CH=CH_2$ |
| CS-9 | 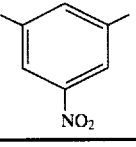 3,5-dinitrophenyl | 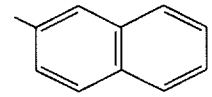 2-naphthyl | 11 | $-CH=CH_2$ |

CS-8 and CS-9 proved to be inferior to CS-7 in terms of their ability to separate the enantiomers of β-blockers as the data in Table IX shows. In each instance the chiral selector being evaluated was employed as a CSP.

TABLE IX

Separation of the Enantiomers of Some β-Blockers and Analogs on Several of the Second Groups of Chiral Selectors of the Invention

| | CSP-8 | | CSP-9 | | CSP-7 | |
|---|---|---|---|---|---|---|
| Analyte | $\alpha^a$ | $k_1^{'b}$ | $\alpha^a$ | $k_1^{'b}$ | $\alpha^a$ | $k_1^{'b}$ |
| Metroprolol | 1.00 | 2.09 | 1.00 | 2.32 | 1.28 | 3.14 |
| | | | | | 1.08* | 6.37* |
| Oxprenolol | 1.00 | 4.87 | 1.00 | 4.44 | 1.35 | 4.79 |
| | | | | | 1.15* | 7.16* |
| Pronethalol | 1.00 | 3.36 | 1.00 | 3.24 | 1.04 | 4.77 |
| | | | | | 1.00* | 7.83* |
| Propranolol | 1.15 | 3.27 | 1.23 | 2.78 | 2.15 | 4.64 |
| | | | | | 1.28* | 8.52* |
| Pindolol | 1.15 | 11.73 | 1.20 | 7.86 | 2.27 | 10.44 |
| | | | | | 1.38* | 9.67* |
| Bufuralol | 1.14 | 1.62 (+)(R)** | 1.20 | 1.38 (+)(R)** | 1.89 | 1.85 (+)(R)** |
| | | | | | 1.19* | 3.25* |
| 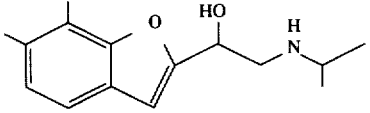 | 1.20 | 2.14 | 1.25 | 1.86 | 2.27 | 2.97 |
| | | | | | 1.29* | 4.73* |
| 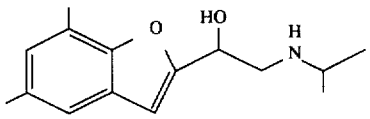 | 1.18 | 2.10 | 1.25 | 1.85 | 2.25 | 2.93 |
| | | | | | 1.31* | 4.70* |
| 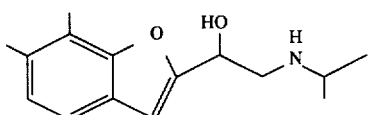 | 1.27 | 2.58 | 1.35 | 2.10 | 2.96 | 3.36 |
| | | | | | 1.53* | 5.82* |

<sup>a</sup>Chromatographic separation factor.
<sup>b</sup>The capacity factor using $CH_2Cl_2$:EtOH = 19:1 with 0.5 g/L of $NH_4OAC$ as the mobile phase at a flow rate of 2 mL/min.
*Data using CH3CN:EtOH = 9:1 containing 0.5 g/L of $NH_4OAC$ as the mobile phase at a flow rate of 2 mL/min.
**The absolute configuration of the more strongly retained enantiomer.

There are parallels in the behaviors of phosphonate CS-6 and β-lactam CS-7 when employed as CSPs. Both show increased enantioselectivity for β-blockers as well as the unusual effect of reduced retention and improved band shapes as column temperature is reduced (compare data in Tables IX and X). The latter effects are keyed to the presence of the ammonium acetate which is suspected of serving to protonate the β-blockers as well as possibly being a competitor for binding sites on the CSP. Whatever the origin of the effect, the ammonium acetate more effectively reduces the retention of the less retained enantiomer than it does the more retained enantiomer as the temperature is reduced to 0° C. This is a very desireable situation for both analytical and preparative scale separations.

TABLE X

The Effect of Temperature on Retention and Enantioselectivity for Some of β-Blockers and Analogs Using CSP-7

| Analyte | 24° C. $\alpha^a$ | 24° C. $k_1$,$^b k_2$ | 0° C. $\alpha^a$ | 0° C. $k_1$,$^b k_2$ | −10° C. $\alpha^a$ | −10° C. $k_1$,$^b k_2$ |
|---|---|---|---|---|---|---|
| Metoprolol | 1.31 | 4.44 5.82 | 1.59 | 2.25 3.58 | 1.81 | 1.84 3.32 |
| Oxprenolol | 1.37 | 5.32 7.31 | 1.74 | 2.99 5.19 | 2.01 | 2.40 4.82 |
| Pronethalol | 1.03 | 6.97 7.18 | 1.00 | 4.89 4.89 | 1.00 | 4.42 4.42 |
| Propranolol | 2.16 | 6.03 13.01 | 3.19 | 3.91 12.46 | 4.02 | 3.58 14.40 |
| Pindolol | 2.41 | 13.97 33.72 | 3.94 | 10.07 39.64 | 4.73 | 8.91 42.18 |
| Bufuralol | 1.92 | 2.54 4.87 | 2.93 | 1.76 5.14 | 3.66 | 1.64 6.01 |
| 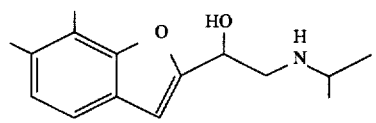 | 2.30 | 4.27 9.85 | 3.51 | 3.41 11.96 | 4.13 | 3.13 12.94 |
| 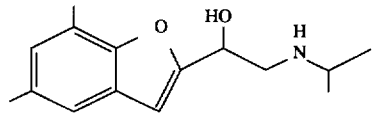 | 2.28 | 4.05 9.26 | 3.43 | 3.22 11.07 | 4.11 | 2.99 12.31 |
| 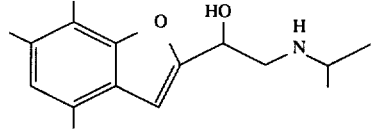 | 3.09 | 4.79 14.83 | 4.80 | 4.28 20.54 | 5.82 | 4.20 24.45 |
| 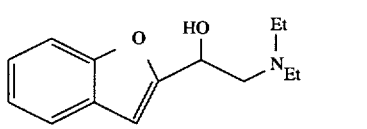 | 1.00 | 1.62 1.62 | 1.00 | 1.70 1.70 | 1.15 | 1.55 1.78 |
| O-Methyl propranolol | 1.19 | 3.32 3.95 | 1.22 | 2.62 3.18 | 1.25 | 2.52 3.14 |
| O-Methyl, N-formyl propranolol | 1.15 | 3.85 4.42 | 1.24 | 2.91 3.61 | 1.26 | 2.66 3.34 |

$^a$Chromatographic separation factor.
$^b$The capacity factor using 19:1 $CH_2Cl_2$:EtOH with 0.5 g/L of $NH_4OAc$ as the mobile phase at a flow rate of 2 mL/min.

What is claimed is:
1. A chemical compound having the formula:

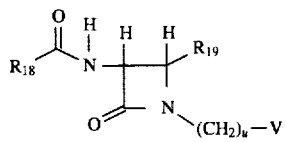

wherein
$R_{18}$ is

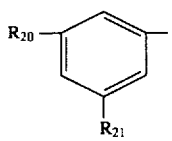

$R_{19}$ is lower alkyl or aryl,
$R_{20}$ and $R_{21}$ are each independently $NO_2$, $N(R_{22})_3^+$, CN, $COOR_{23}$, $SO_3H$ or $COR_{24}$,
$R_{22}$, $R_{23}$ and $R_{24}$ are each independently hydrogen or lower alkyl,
V is H or $CH=CH_2$, and
U is 1 to 20, said compound being an R or an S enantiomer or a mixture of R and S enantiomers.

2. The compound of claim 1 wherein
$R_{18}$ is

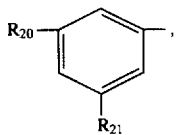

$R_{19}$ is phenyl, t-butyl or α-naphthyl, and
$R_{20}$ and $R_{21}$ are each $NO_2$.

3. The compound of claim 2 wherein
$R_{19}$ is phenyl,
V is $CH=CH_2$, and
u is 1.

4. An LC column wherein the stationary phase comprises an R or an S enantiomer of the compound of claim 3 immobilized on a support effective for use in chromatographic separation.

5. A method of producing a stationary phase for an LC column which comprises immobilizing an R or an S enantiomer of the compound of claim 3 n a support effective for use in chromatographic separation.

6. The compound of claim 2 wherein
$R_{19}$ is phenyl,
V is hydrogen, and
u is 3.

7. The compound of claim 2 wherein
$R_{19}$ is t-butyl,
V is $CH=CH_2$, and
u is 11.

8. The compound of claim 2 wherein
$R_{19}$ is t-butyl,
V is hydrogen and
u is 11.

9. The compound of claim 2 wherein
$R_{19}$ is α-naphthyl,
V is $CH=CH_2$, and
u is 11.

10. The compound of claim 2 wherein
$R_{19}$ is α-naphthyl,
V is H, and
u is 11.

11. A process of separating enantiomers which comprises contacting a mixture of enantiomers of a first compound having a first and a second optical configuration and having the formula:

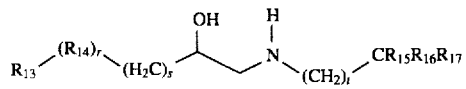

wherein
$R_{13}$ is aryl or a nitrogen, sulfur or oxygen containing heterocyclic ring, either of which may be unsubstituted or substituted with lower alkyl, lower alkoxyalkyl or lower alkenyloxy,
$R_{14}$ is O, S or NH,
$R_{15}$, $R_{16}$ and $R_{17}$ are each independently hydrogen or lower alkyl, and
r, s and t are independently 0 or 1,
with a chiral selector, said selector being an R or S enantiomer of the compound of claim 1, under conditions effective to form a complex between an enantiomer of said first compound having said first optical configuration and an enantiomer of said compound of claim 1 and recovering the non-complexed enantiomer of said first compound having said second optical configuration.

12. A process according to claim 11 including the additional step of:
subjecting the complex to conditions effective to dissociate the enantiomer of said first compound having said first optical configuration from the enantiomer of said first compound of claim 1 and
recovering the enantiomer of said first compound having said first optical configuration.

13. A process according to claim 11 wherein the stationary phase in an LC column comprises said chiral selector and the less retained enantiomer of said first compound having said second optical configuration elutes from said column prior to said first compound having said first optical configuration.

14. A process according to claim 13 wherein
$R_{18}$ is

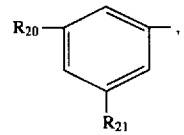

$R_{19}$ is phenyl,
$R_{20}$ and $R_{21}$ are each $NO_2$,
V is $CH=CH_2$, and
u is 1.

15. The process according to claim 11 wherein a liquid membrane comprising said chiral selector is passed in contact with one side of a semi-permeable membrane and said mixture of enantiomers of said first compound is in contact with the other side of said semi-permeable membrane.

16. A process according to claim 15 wherein $R_{18}$ is

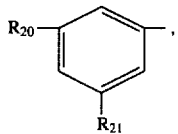

$R_{19}$ is phenyl, $R_{20}$ and $R_{21}$ are each $NO_2$,

V is H, and u is 3.

17. A process according to claim 14 or 16 wherein $R_{13}$ is

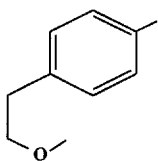

$R_{14}$ is O;

r and s are each 1 and t is 0; and $R_{15}$ is H and $R_{16}$ and $R_{17}$ are each $CH_3$.

18. A process according to claim 14 or 16 wherein $R_{13}$ is

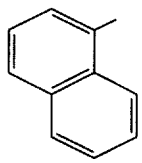

$R_{14}$ is O;

r and s are each 1 and t is 0; and $R_{15}$ is H and $R_{16}$ and $R_{17}$ are each $CH_3$.

19. A process according to claim 14 or 16 wherein $R_{13}$ is

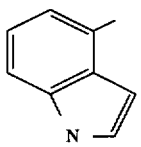

$R_{14}$ is O;

r and s are each 1 and t is 0; and $R_{15}$ is H and $R_{16}$ and $R_{17}$ are each $CH_3$.

20. A process according to claim 14 or 16 wherein $R_{13}$ is

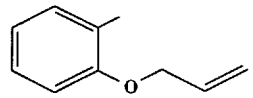

$R_{14}$ is O;

r and s are each 1 and t is 0; and $R_{15}$ is H and $R_{16}$ and $R_{17}$ are each $CH_3$.

21. A process according to claim 14 or 16 wherein $R_{13}$ is

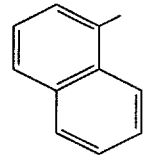

r, s and t are each 0; and $R_{15}$ is H and $R_{16}$ and $R_{17}$ are each $CH_3$.

22. A process according to claim 14 or 16 wherein $R_{13}$ is

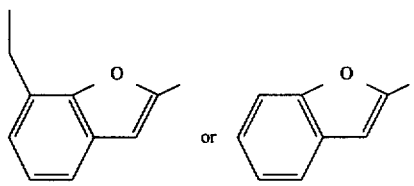

r, s and t are each 0;

$R_{15}$ and $R_{16}$ are each independently H or $CH_3$; and $R_{17}$ is $CH_3$ or $$CH\begin{matrix}CH_3\\CH_3\end{matrix}.$$

23. An LC column wherein the stationary phase comprises an R or an S enantiomer of the compound of claim 1 immobilized on a support effective for use in chromatographic separation.

24. A method of producing a stationary phase for an LC column which comprises immobilizing an R or an S enantiomer of the compound of claim 1 on a support effective for use in chromatographic separation.

25. The compound of claim 1 wherein $R_{19}$ is t-butyl, phenyl or α-naphthyl.

26. The compound of claim 1 wherein $R_{20}$ and $R_{21}$ are each independently $NO_2$.

27. The compound of claim 1 wherein $R_{22}$, $R_{23}$, and $R_{24}$ are each independently hydrogen or methyl.

28. The compound of claim 1 wherein V is H and U is 1 to 11.

29. The compound of claim 1 wherein V is CH=$CH_2$ and U is 1 to 9.

UNITED STATES PATENT AND TRADEMARK OFFICE
CERTIFICATE OF CORRECTION

PATENT NO. : 5,578,212                           Page 1 of 2
DATED      : November 26, 1996
INVENTOR(S): William H. Pirkle, et al.

It is certified that error appears in the above-indentified patent and that said Letters Patent is hereby corrected as shown below:

On the Title Page, after "Section [22]..." has been modified to read -- [30] Foreign Application Priority Data PCT/US92/07878 9-17-92 --

Column 5, line 1, "and $R_2 R_3$" should read --$R_2$ and $R_3$--

Column 6, line 33: "are is a plots" should read --are plots--

Column 6, line 36: "are is a plot" should read --are plots--

Column 7, line 55: delete "5"

Column 11, line 1: "2-2" should read --2-2'--

Column 11, line 55, Table III: "$CH_3 CH=CH_2$" should read --$CH_2 CH=CH_2$--

Column 12, line 55, Table III: "$CH_3 CH=CH_2$" should read --$CH_2 CH=CH_2$--

Column 16, line 37: "Enantismers" should read --Enantiomers--

Column 16, line 47: "$CH_2$" should read --$CH_3$--

Column 16, line 55: "B" should read -- $\mathcal{B}$ --

Column 21, line 10: "13.1" should read --3.1--

UNITED STATES PATENT AND TRADEMARK OFFICE
CERTIFICATE OF CORRECTION

PATENT NO. : 5,578,212

DATED : November 26, 1996

INVENTOR(S) : William H. Pirkle, et al.

It is certified that error appears in the above-indentified patent and that said Letters Patent is hereby corrected as shown below:

Column 21, line 65: " $^1$H" should read -- $_1$H--

Column 22, line 39: " $^1$H" should read -- $_1$H--

Signed and Sealed this

Fourth Day of November, 1997

Attest:

BRUCE LEHMAN

Attesting Officer

Commissioner of Patents and Trademarks